(12) United States Patent
Vaughan

(10) Patent No.: US 9,568,572 B2
(45) Date of Patent: Feb. 14, 2017

(54) BANDAGE OR GARMENT COMBINED WITH A WIRELESSLY COUPLED MAGNETIC RESONANCE COIL

(75) Inventor: J. Thomas Vaughan, Stillwater, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 333 days.

(21) Appl. No.: 11/429,463

(22) Filed: May 5, 2006

(65) Prior Publication Data

US 2006/0279284 A1  Dec. 14, 2006

Related U.S. Application Data

(60) Provisional application No. 60/678,759, filed on May 6, 2005.

(51) Int. Cl.
| | | |
|---|---|---|
| *G01R 33/345* | (2006.01) | |
| *A61B 5/055* | (2006.01) | |
| *G01R 33/36* | (2006.01) | |
| *A61B 5/05* | (2006.01) | |
| *G01R 33/34* | (2006.01) | |

(52) U.S. Cl.
CPC ............. *G01R 33/3692* (2013.01); *A61B 5/05* (2013.01); *G01R 33/345* (2013.01); *G01R 33/34007* (2013.01)

(58) Field of Classification Search
USPC .. 324/218, 300–322; 600/407–435; 336/200, 83, 65; 382/128–131
See application file for complete search history.

(56) References Cited

U.S. PATENT DOCUMENTS

| | | | |
|---|---|---|---|
| 5,245,288 A | 9/1993 | Leussler | |
| 5,384,536 A | 1/1995 | Murakami et al. | |
| 5,545,999 A | 8/1996 | Mueller et al. | |
| 5,666,055 A | 9/1997 | Jones et al. | |
| 5,676,673 A * | 10/1997 | Ferre et al. .................... | 606/130 |
| 5,841,278 A * | 11/1998 | Green ................ | G01R 33/3657 324/318 |
| 6,011,393 A * | 1/2000 | Kaufman et al. ............. | 324/318 |
| 6,084,411 A | 7/2000 | Giaquinto et al. | |
| 6,236,205 B1 * | 5/2001 | Ludeke et al. ................ | 324/318 |
| 6,445,271 B1 * | 9/2002 | Johnson ........................ | 336/200 |
| 6,490,557 B1 * | 12/2002 | Jeppesen ....................... | 704/235 |
| 6,498,557 B2 * | 12/2002 | Johnson ........................ | 336/200 |

(Continued)

FOREIGN PATENT DOCUMENTS

| | | |
|---|---|---|
| DE | 4440619 | 8/1995 |
| JP | 09-075323 | 3/1997 |

(Continued)

OTHER PUBLICATIONS

International Search Report for corresponding PCT Application No. PCT/US2006/017576, (Aug. 28, 2006), 6 pgs.

(Continued)

*Primary Examiner* — Melissa Koval
*Assistant Examiner* — Tiffany Fetzner
(74) *Attorney, Agent, or Firm* — Quarles & Brady LLP

(57) ABSTRACT

This document discusses, among other things, a radio frequency magnetic coil is coupled to a wireless communication circuit. The wireless communication circuit allows control or monitoring of individual channels or other functions of a coil.

28 Claims, 4 Drawing Sheets

(56) References Cited

U.S. PATENT DOCUMENTS

| | | | | |
|---|---|---|---|---|
| 6,684,091 | B2* | 1/2004 | Parker | A61B 5/14552 600/310 |
| 6,925,322 | B2* | 8/2005 | Helfer et al. | 600/423 |
| 6,961,604 | B1* | 11/2005 | Vahasalo et al. | 600/410 |
| 6,980,848 | B2* | 12/2005 | Helfer et al. | 600/423 |
| 7,389,137 | B2* | 6/2008 | Helfer et al. | 600/423 |
| RE41,317 | E* | 5/2010 | Parker | A61B 5/14552 600/310 |
| 7,885,700 | B2* | 2/2011 | Clark | G01R 29/12 600/372 |
| RE43,169 | E* | 2/2012 | Parker | A61B 5/14552 600/310 |
| RE44,823 | E* | 4/2014 | Parker | A61B 5/14552 600/310 |
| 2001/0029325 | A1* | 10/2001 | Parker | A61B 5/14552 600/344 |
| 2002/0057173 | A1* | 5/2002 | Johnson | 336/200 |
| 2002/0151788 | A1* | 10/2002 | Menon | 600/421 |
| 2003/0078004 | A1 | 4/2003 | Vester | |
| 2004/0019273 | A1* | 1/2004 | Helfer et al. | 600/422 |
| 2004/0054278 | A1 | 3/2004 | Kimchy et al. | |
| 2004/0124838 | A1* | 7/2004 | Duerk et al. | 324/304 |
| 2005/0107681 | A1* | 5/2005 | Griffiths | 600/410 |
| 2005/0197563 | A1* | 9/2005 | Helfer et al. | 600/410 |
| 2005/0203378 | A1* | 9/2005 | Helfer et al. | 600/410 |
| 2006/0058694 | A1* | 3/2006 | Clark | G01R 29/12 600/509 |
| 2006/0279284 | A1* | 12/2006 | Vaughan | 324/318 |
| 2007/0161884 | A1* | 7/2007 | Black et al. | 600/407 |
| 2008/0204021 | A1* | 8/2008 | Leussler et al. | 324/318 |
| 2009/0248112 | A1* | 10/2009 | Mumbru et al. | 607/60 |

FOREIGN PATENT DOCUMENTS

| | | |
|---|---|---|
| WO | WO-01/75466 A1 | 10/2001 |
| WO | WO-02/31522 A1 | 4/2002 |
| WO | WO-03032002 A1 | 4/2003 |
| WO | WO-03/093852 A1 | 11/2003 |
| WO | WO-2005/024448 A1 | 3/2005 |
| WO | WO-2005/052621 A1 | 6/2005 |
| WO | WO-2006/000928 A2 | 1/2006 |

OTHER PUBLICATIONS

Morikawa, S., et al., "Long-Term Observation of In Vivo $^{31}$P NMR Spectra in Carbon Tetrachloride-Intoxicated Rabbit Liver Using Implanted Wireless Surface Coil", *NMR in Biomedicine*, 8(1), (Feb. 1995), 3-8.

* cited by examiner

BANDAGE OR GARMENT COMBINED WITH A WIRELESSLY COUPLED MAGNETIC RESONANCE COIL

CROSS-REFERENCE TO RELATED PATENT DOCUMENTS

This patent application claims the benefit of priority, under 35 U.S.C. Section 119(e), to Vaughan U.S. Provisional Patent Application Ser. No. 60/678,759, entitled "WIRELESSLY COUPLED MAGNETIC RESONANCE COIL," filed on May 6, 2005, and is incorporated herein by reference.

TECHNICAL FIELD

This document pertains generally to magnetic resonance, and more particularly, but not by way of limitation, to a wirelessly coupled magnetic resonance coil.

BACKGROUND

Magnetic resonance (MR) coils are used for biomedical and other applications. The coils are used in magnetic resonance imaging (MRI) as well as magnetic resonance spectroscopy (MRS), electron paramagnetic resonance (EPR) and electron spin resonance (ESR), functional MRI (fMRI) and other magnetic resonance modalities.

Some magnetic resonance coils, such as a multi-channel parallel imaging coil, have 96 or more discrete channels some of which include multiple RF signal lines, power supply lines, control lines, physiological monitoring lines, communication lines, physiological stimuli lines and other electrically conductive or optically conductive lines and cables.

Each channel of a multi-channel radio frequency (RF) coils used for MR applications is electrically connected to a driver circuit, receiver circuit, or both a driver and receiver circuit. In addition, multiple cables, power lines and control lines combine to make an unwieldy bundle of cables that can impair the medical procedure. In particular, with a large number of cables, the ease of use, flexibility, versatility, quality of performance and ergonomics of the coil are reduced. Signal losses are also a problem with the long cables required.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the present subject matter may be practiced. These embodiments, which are also referred to herein as "examples," are described in enough detail to enable those skilled in the art to practice the present subject matter. The embodiments may be combined, other embodiments may be utilized, or structural, logical and electrical changes may be made without departing from the scope of the present subject matter. The following detailed description is, therefore, not to be taken in a limiting sense, and the scope of the present subject matter is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

An embodiment of the present subject matter includes a magnetic resonance coil configured for wireless communication with a remote transceiver element coupled to a magnetic resonance system. A coil includes one or more wireless links which provide an electrical connection for such lines as RF signal, power, control, sensor and physiological monitoring and other conductive and fiber optic lines.

Figure 1:
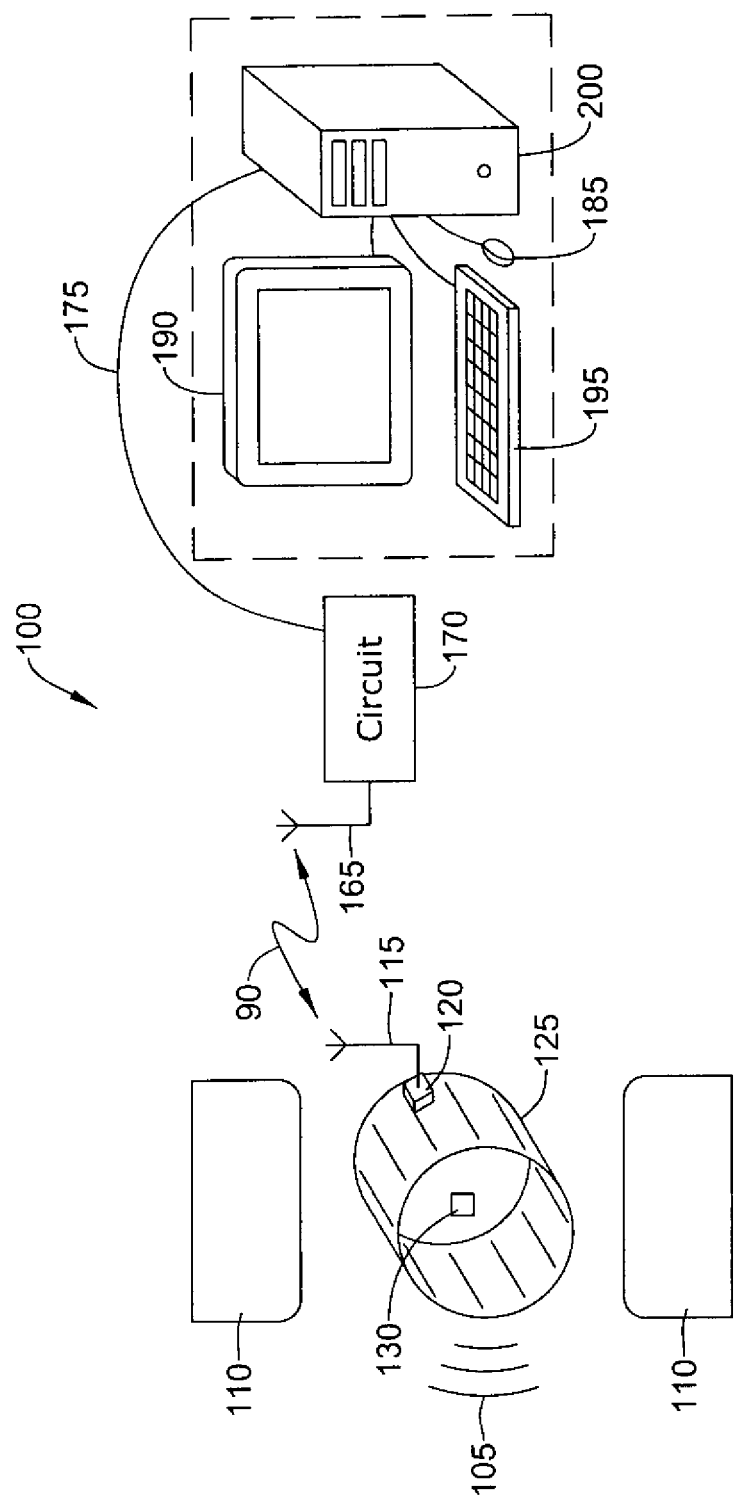
FIG. 1 schematically illustrates a magnetic resonance system having a wirelessly coupled coil.

FIG. 1 includes an illustration of system 100. System 100 includes main magnet 110 which generates a $B_0$ magnetic field 105 for imaging or spectroscopy. Disposed within magnetic field 105 is radio frequency coil 125. In the example illustrated, coil 125 is a volume coil configured for imaging a specimen within region of interest 130. Coil 125 is illustrated as a transverse electro-magnetic (TEM) coil, however other types of coils can also be used, including for example, birdcage structures and Helmholz coils and phased array and parallel arrays. Coil 125 includes a number of parallel current elements, each of which is coupled to wireless circuit 120. Wireless circuit 120 is coupled to antenna 115. In various examples, circuit 120 includes a transmitter, a receiver or a transceiver.

As used herein, the coil can include a plurality of current elements where each current element includes a segment of a transmission line. As such, the current element can include a pair of conductors separated by a dielectric, a waveguide, a coaxial conductor segment or other transmission line.

Circuit 170 includes a wireless communication circuit which, in various examples, include a transmitter, a receiver or a transceiver. Circuit 170 is coupled to antenna 165 which is in wireless communication with antenna 115 via link 90. Link 90, in one example include an optical coupling such as an infrared channel.

Circuit 170 is coupled to computer system 180 by wired connection 175. Computer system 180 includes monitor 190, processor 200 and user input devices including mouse 185 and keyboard 195. Computer system 180, in one example, is coupled to a communication network (not shown) which facilitate remote operation.

In various examples, the RF coil includes an on-board transmitter, receiver or transceiver which communicates with the MR system by a wireless communication protocol.

The coil can be configured for placement on a patient while in an examining room or dressing room and worn, or carried on the body, into the MR magnet for an MR scan. In one example, wireless nanotechnology is used to introduce or implant one or more biocompatible coils into body cavities, blood vessels, orifices or into organs, tissues, or tumors without requiring a connection by means of a wire, cable or an optical fiber. The coil, in one example, includes an adhesive coated surface that bonds to a skin surface. Individual elements of the coil can be fabricated on a flexible substrate using semiconductor fabrication technology. In one example, the present subject matter includes a wireless coil in the form of a bandage.

Figure 2:
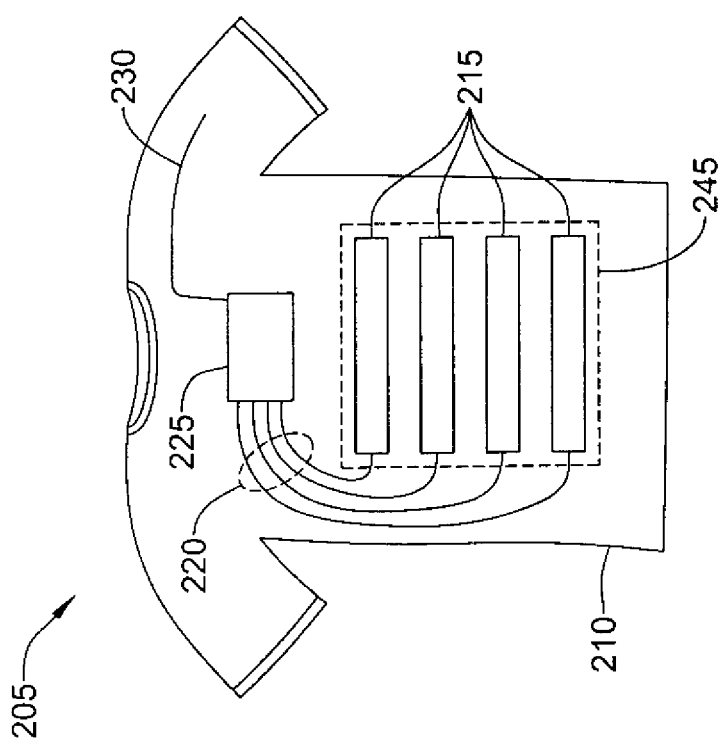
FIG. 2 illustrates a garment configured with a wireless coil.

FIG. 2 illustrates a garment configured according to the present subject matter. In the figure, system 205 includes garment 210 having coil 245 affixed thereon. Coil 245 is illustrated as a surface coil having four TEM segments 215 arranged in a planar configuration. Other coils are also contemplated, including, for example, a volume coil or phased array. Each coil segment 215 is coupled to wireless circuit 225 by connector bundle 220. Each coil segment can have its own dedicated nanotech transmitter or receiver. Wireless circuit 225 is coupled to antenna 230. Antenna 230 is also affixed to the garment. Circuit 225 can be powered by a battery or by passive excitation. The coil, or coil segments, can be affixed to the garment by stitching, adhesives, mechanical fasteners, or other means. In one example, the garment includes a fabric structure configured to be worn on a body.

Figure 3:
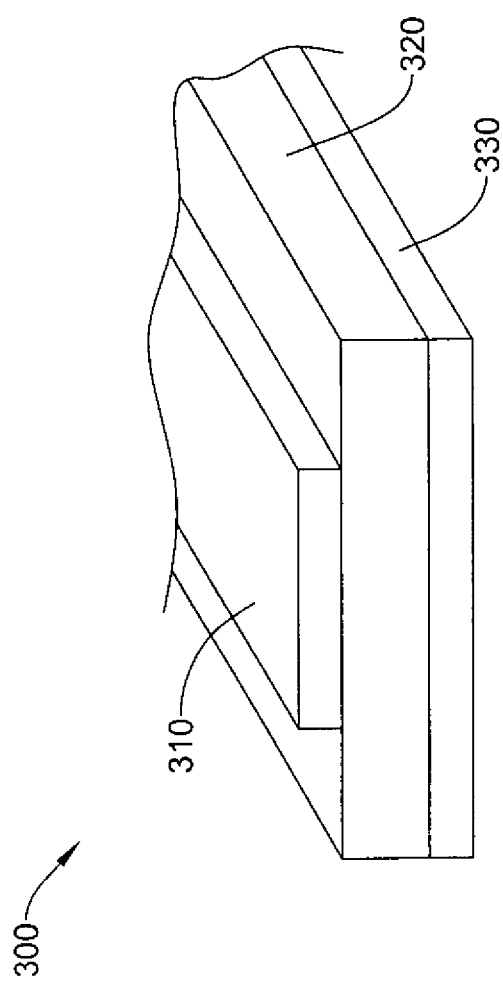
FIG. 3 illustrates an exemplary current element.

FIG. 3 illustrates a portion of current element 300 according to one example of the present subject matter. In the figure, current element 300 includes first conductive member 310, dielectric 320 and second conductive member 330. A transverse electromagnetic wave resonates in current element 300 based on various parameters including the dimensions and physical properties of the structure and can be controlled by various methods.

Figure 4:
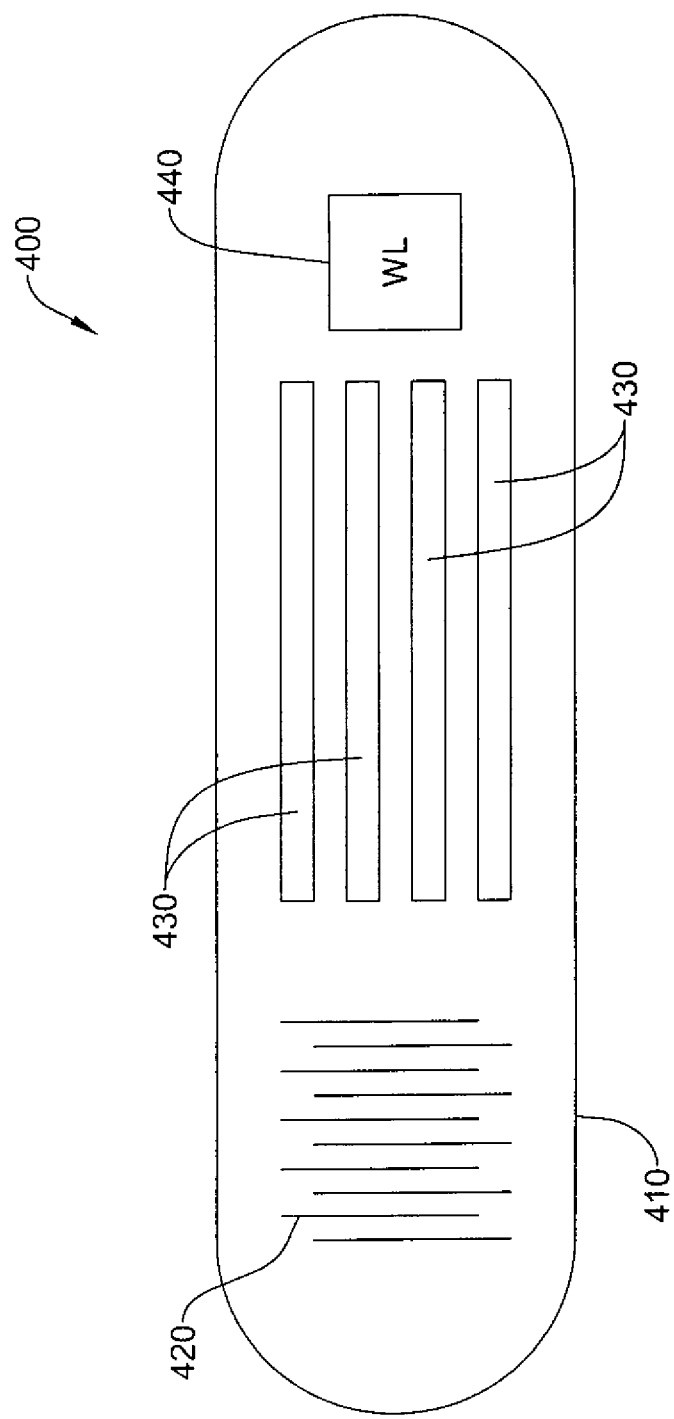
FIG. 4 illustrates an example of a passive coil.

FIG. 4 illustrates apparatus 400 according to the present subject matter. In the figure, power supply 420 is illustrated in the form of a passive interdigitated element. In other examples, power supply 420 includes a battery, such as a rechargeable battery. Current elements 430 are disposed about a region and can be in the form of a volume, surface or other type of coil. In addition to TEM coils, other types are also contemplated, including bird cage coils. Wireless communication module 440 allows apparatus 400 to communicate with an interface coupled to a magnetic resonance system. Enclosure 410, in various examples, includes a bio-compatible housing or structure. In various examples, enclosure 410 includes a pill configured for ingestion or implantation using a surgical procedure.

In one example, a wireless RF coil facilitates signal and communication links from multiple components of an MR system or from multiple MR systems which may be nearby or in a remote location. For example, an adhesive-attached coil affixed to a particular patient can be used to generate a first image using a first magnetic resonance system and at a later time, a second image can be generated using a second magnetic resonance system. The adhesive-attached coil can remain affixed to a skin surface for an extended period of time amounting to days, weeks, months or years. In one example, a coil can be implanted or disposed in a body cavity for an extended period of time where the coil is passively powered or battery powered.

The present subject matter can be configured for use in clinical or research systems as well as animal, chemical, pharmaceutical, food processing and down hole oil well logging and other markets.

Wireless protocols used in the telecommunication industry can be adapted for use with the present subject matter. Examples of protocols include those established by standards and regulatory bodies such as the Federal Communications Commission (FCC), Mobile IP (a proposed standard protocol), Internet Engineering Task Force (IETF) and the Internet Engineering Steering Group (IESG), Pacific Telecommunications Council (PTC), International Standards Organization (ISO), International Telecommunication Union (ITU) and the National Telecommunications and Information Administration (NTIA). Specific examples of protocols include 3G (third generation), Bluetooth, Groupe Spécial Mobile (GSM), General Packet Radio Service (GPRS), Enhanced Data rates for GSM Evolution (EDGE) and third generation GSM services (3GSM*), Universal Mobile Telecommunications System (UMTS), Code Division Multiple Access (CDMA), wideband CDMA (WCDMA), Institute of Electrical and Electronics Engineers, Inc (IEEE) 802.11 and Ultra wideband (UWB).

Wireless communication can be conducted using any of a variety of portions of the electromagnetic spectrum. For example, in addition to radio frequency communication, the present subject matter can be configured for operation using various types of radiation including infrared, visible or ultrasonic signaling.

Multi-channel radio frequency coils for MRI applications require multiple RF signal and control cables, typically to every channel in a multiple channel coil and MR system. This multiplicity of cables, power lines, and control lines often makes an unwieldy bundle limiting the overall ease of use, flexibility, versatility, quality of performance, and ergonomics of an RF coil for biomedical or other MR applications.

The present subject matter provides a means to replace hard wired (connected) RF signal lines, power lines, control lines, physiological monitoring lines, and other conductive and fiber optic lines.

The coil includes a transmitter, receiver, or transceiver in wireless communication with the MR system to eliminate some or all wires and cables connecting the coil to the system. This allows, for example, a coil to be conveniently placed on a patient in an examining or dressing room, and then "worn" into the vicinity of the MR magnet for an MR scan. Additionally, wireless nanotechnologies allows introduction or implantation of sterile coils into body cavities, blood vessels, orifices, or into organs, tissues, or tumors without the need to connect it to outside of the body by means of wire, cable, or optic fiber.

The present subject matter can be used for biomedical MR imaging, MR spectroscopy, echo planar imaging (EPI), electron spin resonance (ESR), functional MR imaging (fMRI) as well as other magnetic resonance modalities.

Certain MR techniques and technology, such as parallel imaging using multiple channels (sometimes 96 channels or more) require that an RF coil be connected to an MR system by multiple RF signal lines, power supply lines, control lines, physiological monitoring lines, communications lines, physiological stimuli lines, and other possible conductive (wire) or optical lines and cables.

A wireless connection between the coil and the MR system allows multiple channels without the encumbrances, constraints, and problems associated with multiple hard wired connections. In addition, a wireless coil facilitates signal and communication links with the RF coil from multiple components of an MR system or multiple MR systems, nearby or remotely sited.

In one example, selected elements of the telecommunications industry are adapted for use with the present subject matter.

For example, a wireless link can include one or more infrared communication channels or Bluetooth communication channels. Bluetooth refers to a relatively short range wireless protocol using an unlicensed industrial/scientific/medicine (ISM) frequency band.

ADDITIONAL EXAMPLES

In one example, the coil of the present subject matter is affixed to a garment by a stitch, mechanical fastener, adhesive or other means. The coil can be inserted into a pocket or hem of the garment or affixed in a removable manner.

In one example, the coil of the present subject matter is configured to communicate with more than one magnetic resonance system. In such a configuration, the coil is operable with any of a plurality of wireless interfaces, each coupled to a different magnetic resonance system.

In one example, a wireless interface is coupled to a magnetic resonance system and the interface provides interoperability with a plurality of wireless coils, some of which operate according to different protocols or communication modes. In one example, the magnetic resonance system is configured to allow the user to select one of a plurality of coils worn by a particular patient where each coil is in wireless communication with the system.

In one example, the coil is operable at a plurality of resonant frequencies where the frequency is manually selectable or selectable by wireless control. For example, a signal from the wireless interface allows selection of one of a plurality of frequencies. In addition, other examples provide that a phase, a current, or a voltage of a signal can be selected manually or wirelessly.

In addition to controlling one or more selected operating parameters, one example provides that a voltage, a current, a phase or a frequency in the coil can be monitored wirelessly.

In one example, a signal in the coil can be turned off or on wirelessly based on a signal received from the wireless interface and coupled to a magnetic resonance system. In one example, a coil can be detuned by means of a signal sent from the wireless interface.

An example of the present subject matter includes a coil controlled by a feedback signal based on monitoring of timing, phase, frequency, voltage or current.

In one example, the present subject matter includes a coil that at least partially encircles a sample or region of interest. In one example the coil is disposed inside of a sample in a manner that encloses or surrounds the coil. As such, a coil can be configured for insertion in a body cavity or vessel or implantation where the coil is placed by a needle, forceps or other insertion means. Exemplary coils include those that can be deployed in a catheter, in an orally administered pill, by a minimally invasive surgical procedure (such as laparoscopy) or by a needle. In various examples, the present subject matter includes a surface mounted wireless coil or a disposable wireless coil.

In one example, the present subject matter includes a wireless coil that can be fitted to a patient and used with any number of different magnetic resonance systems. For example, a coil can be placed surgically in the tissue of a patient and over the course of years, magnetic resonance images can be generated for the patient using any number of different magnetic resonance systems. The coil can be worn by the patient or implanted in the patient.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, various features may be grouped together to streamline the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus the following claims are hereby incorporated into the Detailed Description, with each claim standing on its own as a separate embodiment.

What is claimed is:

1. A radio frequency magnetic resonance coil current element coupled to a bandage and a wireless communication circuit comprising:

at least one magnetic resonance coil current element configured as a volume coil or a surface coil configured for imaging a specimen, a magnetic resonance coil current element including a first conductive element, a second conductive element, and a dielectric element, the first conductive element and the second conductive element being separated by the dielectric element, wherein the at least one current element is configured for transmitting, and/or receiving at least one radio frequency signal to and/or from a region of interest of the specimen;

a wireless communication circuit coupled to the at least one current element, the wireless communication circuit configured to provide a wireless communication link between the at least one current element and a computer system of a magnetic resonance (MR) system that is configured for providing information pertaining to the at least one radio frequency signal, with the wireless communication circuit displacing a volume of space distinct from volumes of space displaced by the first conductive element, the second conductive element, and the dielectric element; and a bandage coupled to the at least one magnetic resonance coil current element and the wireless communication circuit, wherein the bandage includes an adhesive coated surface that permits removably affixing the at least one magnetic resonance coil current element to a skin surface of a subject;

wherein the magnetic resonance coil is disposed proximal to a main magnet of the MR system and the computer system of the MR system is disposed distal to the main magnet of the MR system.

2. The coil of claim 1 wherein the wireless communication circuit includes at least one of a transmitter, a receiver, and a transceiver.

3. The coil of claim 1 wherein the at least one magnetic resonance coil current element includes a transmission line.

4. The coil of claim 1 further comprising an antenna coupled to the wireless communication circuit.

5. The coil of claim 1 wherein the at least one magnetic resonance coil current element is configured for receiving a radio frequency signal from a region of interest.

6. The coil of claim 1 wherein the at least one magnetic resonance coil current element is configured for transmitting a radio frequency signal to a region of interest.

7. The coil of claim 1 wherein the wireless communication circuit is configured to communicate with at least one magnetic resonance system.

8. The coil of claim 1 wherein the at least one magnetic resonance coil current element is configured for resonance at a frequency that is selected based on a signal received from the wireless communication circuit.

9. The coil of claim 1 wherein a parameter corresponding to a transverse electromagnetic signal in the at least one magnetic resonance coil current element is selected based on a control signal received from the wireless communication circuit.

10. The coil of claim 9 wherein the parameter includes at least one of a phase, a current, and a voltage.

11. The coil of claim 9 wherein the transverse electromagnetic signal can be detuned based on the control signal received from the wireless communication circuit.

12. The coil of claim 1 wherein a parameter corresponding to a transverse electromagnetic signal in the at least one magnetic resonance coil current element is monitored based on a control signal received from the wireless communication circuit.

13. The coil of claim 12 wherein the parameter includes at least one of a current, a voltage, a frequency, and a phase.

14. The coil of claim 1 wherein a transverse electromagnetic signal in the at least one magnetic resonance coil current element is controlled by a feedback signal generated as a function of a monitored parameter, wherein the monitored parameter is monitored wirelessly, and the feedback signal is provided wirelessly.

15. The coil of claim 4 further comprising a second wireless communication circuit in wireless communication with the wireless communication circuit via wireless link.

16. The coil of claim 15 further comprising a second antenna coupled to the second wireless communication circuit.

17. The coil of claim 15 wherein the second wireless communication circuit is coupled to a magnetic resonance computing system.

18. The coil of claim 15 wherein the wireless link is an optical link.

19. The coil of claim 1, wherein the bandage includes a flexible material.

20. The coil of claim 1 wherein the at least one magnetic resonance coil current element and the wireless communication circuit are disposable.

21. The coil of claim 1, wherein the wireless communication circuit includes at least one of a nanotechnology transmitter and a nanotechnology receiver.

22. A method of using a radio frequency magnetic resonance coil current element coupled to a bandage and a wireless communication circuit comprising:
- arranging a radio frequency magnetic resonance coil which is coupled to a bandage that includes an adhesive coated surface configured for removably affixing the radiofrequency magnetic resonance coil onto a skin surface of a subject, and
- having a magnetic resonance coil current element disposed about a region of interest, and proximal a main magnet of a magnetic resonance (MR) system by removably affixing the bandage onto a skin surface proximate the region of interest, the magnetic resonance coil current element including:
  - a first conductive element,
  - a second conductive element, and
  - a dielectric element and being configured for imaging a specimen,
- having the radiofrequency magnetic resonance coil also being coupled to a wireless circuit; and
- wirelessly receiving from the wireless circuit a first radio frequency signal based on a monitored current that is present in the radiofrequency magnetic resonance coil; and
- wirelessly transmitting to the wireless circuit, a second radiofrequency signal corresponding to a current selected for the radiofrequency magnetic resonance coil, the current selected being based on a feedback signal generated from the monitored current of the first radiofrequency signal; and
- repeating the wirelessly receiving and transmitting of the first and second radio frequency signals until at least a first image is generated by the magnetic resonance system.

23. The method of claim 22, wherein the wireless circuit includes a nanotechnology transmitter, and further comprising the step of transmitting the first radio frequency signal from the nanotechnology transmitter.

24. The method of claim 22, wherein the wireless circuit includes a nanotechnology receiver, and further comprising the step of receiving the second radio frequency signal by the nanotechnology receiver.

25. A magnetic resonance compatible garment with a removably affixed magnetic resonance coil assembly, comprising:
- a magnetic resonance coil assembly comprising:
  - a magnetic resonance coil disposed proximal a main magnet, of a magnetic resonance system, the magnetic resonance coil having a magnetic resonance coil current element configured for imaging a specimen with the magnetic resonance system;
  - a wireless communication circuit coupled to the magnetic resonance coil current element, the wireless communication circuit being configured in order to provide a wireless communication link between the magnetic resonance coil current element and a computer of the magnetic resonance system that is disposed distal to the main magnet, of the magnetic resonance system;
- a garment having an outer surface onto which the magnetic resonance coil assembly is removably affixed; and
- a means for removably affixing the magnetic resonance coil assembly onto the outer surface of the garment.

26. The apparatus of claim 25 wherein the garment includes a fabric structure configured to be worn on a body.

27. The apparatus of claim 25 wherein the magnetic resonance coil includes a plurality of transmission line segments.

28. The apparatus of claim 27 wherein the wireless communication circuit is coupled to each transmission line segment.

* * * * *